(12) United States Patent
Nambu

(10) Patent No.: US 8,057,098 B2
(45) Date of Patent: Nov. 15, 2011

(54) X-RAY CT APPARATUS AND METHOD OF CREATING CORRECTION DATA FOR X-RAY CT

(75) Inventor: Shuya Nambu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/622,237

(22) Filed: Jan. 11, 2007

(65) Prior Publication Data

US 2007/0172020 A1   Jul. 26, 2007

(30) Foreign Application Priority Data

Jan. 12, 2006   (JP) ................. 2006-005043

(51) Int. Cl.
*G01D 18/00* (2006.01)
*G01N 23/083* (2006.01)

(52) U.S. Cl. ......................... 378/207; 378/18

(58) Field of Classification Search .......... 378/204, 378/207, 4–20; 250/252.1, 363.09
See application file for complete search history.

(56) References Cited

U.S. PATENT DOCUMENTS

| | | | |
|---|---|---|---|
| 4,646,334 A * | 2/1987 | Zerhouni | 378/18 |
| 5,909,477 A * | 6/1999 | Crawford et al. | 378/4 |
| 6,325,539 B1 * | 12/2001 | Bromberg et al. | 378/207 |
| 6,600,801 B2 | 7/2003 | Raupach | |
| 2004/0252810 A1 * | 12/2004 | Tsujii | 378/207 |
| 2005/0211889 A1 * | 9/2005 | Varchena et al. | 250/252.1 |
| 2005/0259784 A1 | 11/2005 | Wu et al. | |
| 2006/0027741 A1 * | 2/2006 | Faber et al. | 250/252.1 |
| 2006/0159223 A1 * | 7/2006 | Wu et al. | 378/18 |
| 2007/0110209 A1 * | 5/2007 | Nishide et al. | 378/4 |
| 2007/0140413 A1 * | 6/2007 | Saracen | 378/18 |
| 2008/0226017 A1 * | 9/2008 | Altman et al. | 378/4 |

FOREIGN PATENT DOCUMENTS

| | | |
|---|---|---|
| JP | 9-248301 | 9/1997 |
| JP | 10-192272 | 7/1998 |
| JP | 2002-191591 | 7/2002 |
| JP | 2005-297 | 1/2005 |

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

A helical scanning operation is performed while a bed is moved, so that data by one-time rotation is collected while positional relationships between a detecting system and a phantom relatively are changed. Further, data obtained by scanning an air region and data obtained by scanning a water region are discriminated on the basis of positional information obtained by positioning scanning or the difference between the air and the water in X-ray absorptance, and correction data is created on the basis of the discrimination.

12 Claims, 7 Drawing Sheets

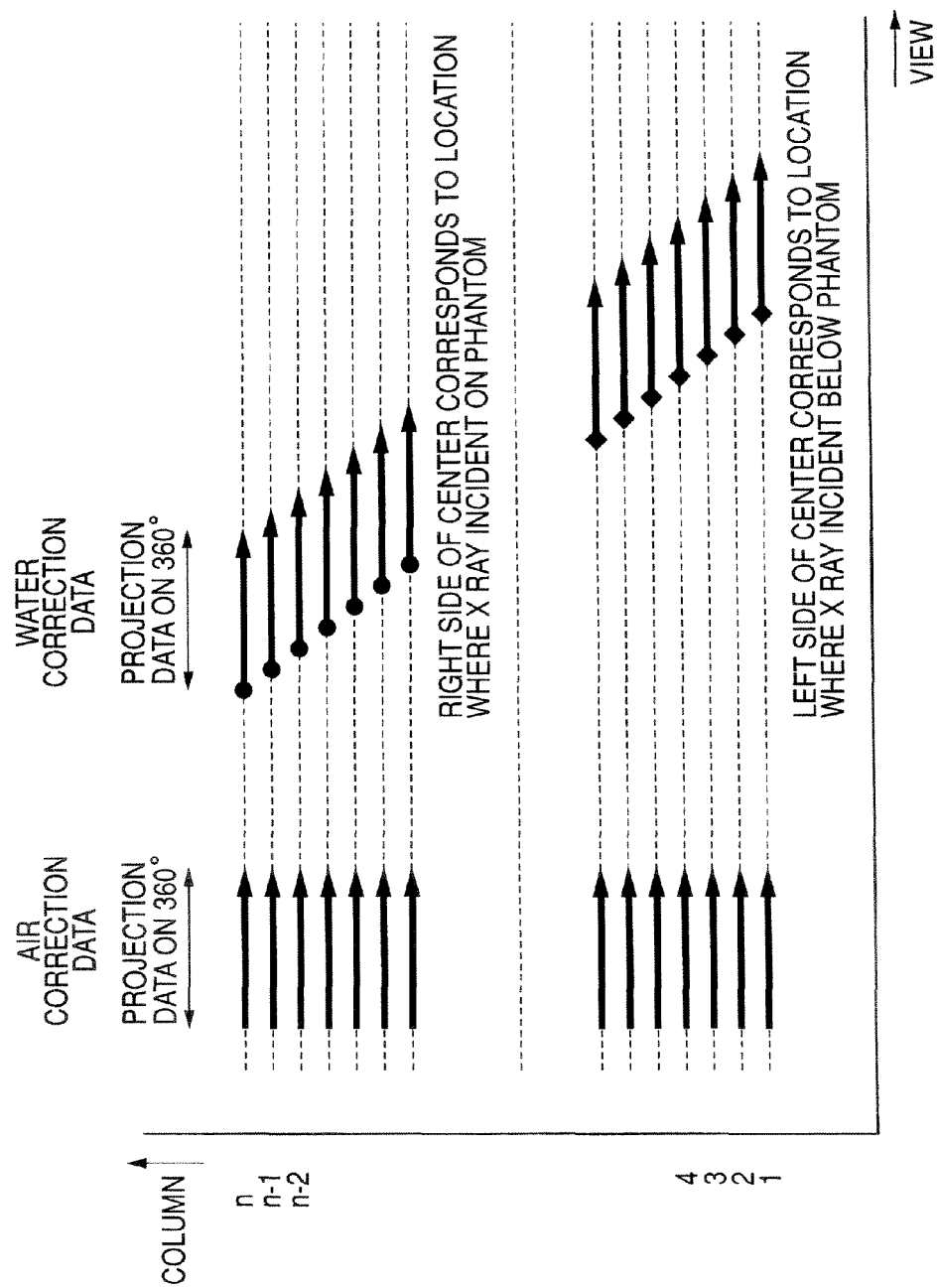

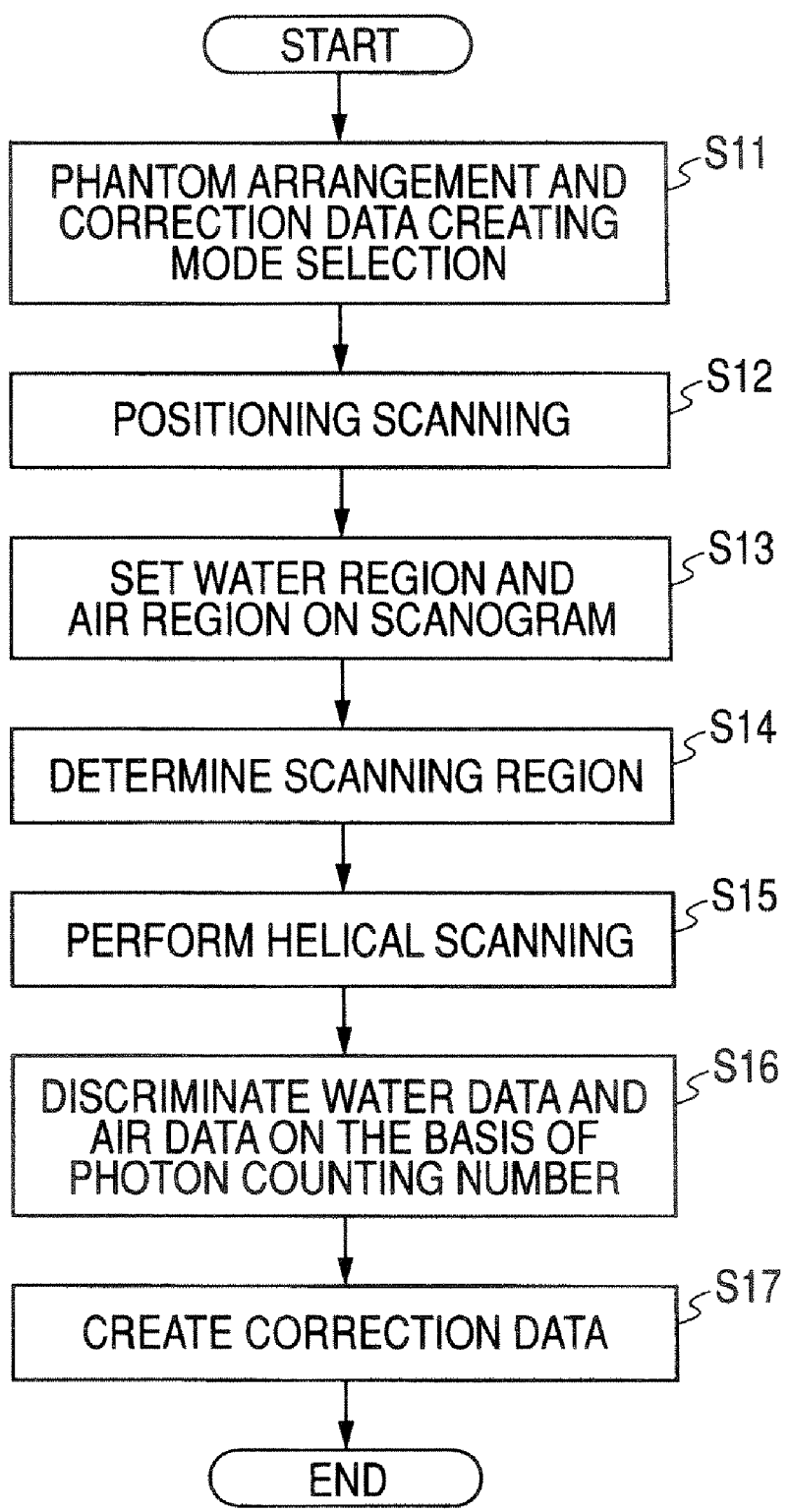

X-RAY CT APPARATUS AND METHOD OF CREATING CORRECTION DATA FOR X-RAY CT

CROSS-REFERENCE TO RELATED APPLICATIONS

This application is based upon and claims the benefit of priority from prior Japanese Patent Application No. 2006-005043, filed Jan. 12, 2006, the entire contents of which are incorporated herein by reference.

BACKGROUND OF THE INVENTION

1. Field of the Invention

The present invention relates to an X-ray CT apparatus having multi-column detectors and a method of creating correction data for X-ray CT, and more particularly, to a technology that is used when creating correction data before photographing a diagnosis image.

2. Description of the Related Art

Generally, X ray CT apparatuses calculate (reconstructs) an X ray absorptance index of tissues, such as internal organs, as indexes or CT values, on the basis of an X ray absorption amount by which X rays are absorbed in a subject, and obtain images (tomographic images). These CT values are generally based on the X ray absorptance of water or air, and are corrected by using correction data so as to correspond to the reference values. Examples of a method of acquiring correction data include a method of acquiring correction data by projecting images again at a plurality of projection angles data from an output image (for example, JP-A-2002-191591), a method of creating a thomographic image from data that is collected by a spiral data collecting unit (for example, JP-A-10-192272), and a method of acquiring data obtained by performing adding and averaging processes on data obtained through rotation of n times as correction data (for example, JP-A-10-248301).

However, the following problems exist in the methods of acquiring correction data according to the related art.

That is, according to the method of acquiring the correction data in the related art, with development of multi-column X-ray detectors (for example, increase in the number of detecting columns), a size of a phantom also needs to be increased. However, it is difficult to set a phantom whose size is increased in a column direction (bed longitudinal direction) to a bed, which causes a large amount of working loads. Further, in order to hold a plurality of phantoms whose diameters are different according to the number of detected columns, a large amount of storage space is required, which is not practical.

Further, according to the methods in the related art, X ray absorptance is acquired by scanning a phantom filled with water. Further, in a state where a photographic subject, such as the phantom or the like, is not disposed, scanning is carried out to obtain X ray absorptance of air. Accordingly, in order to obtain the X ray absorptance of the water or the air, it is necessary to perform a scanning operation twice in a state where the phantom is not disposed and a state where the phantom is disposed, which causes a large amount of working loads.

BRIEF SUMMARY OF THE INVENTION

Accordingly, it is an object of the present invention to provide an X-ray CT apparatus and a method of creating correction data for X-ray CT, in which correction data can be obtained by using a relatively small-sized phantom, and X-ray absorptance of air and water can be obtained by a one-time scanning sequence.

According to an aspect of the present invention, it is provided an X-ray CT apparatus including a projection data collecting unit that continuously moves a ceiling plate mounting a calibration phantom and continuously rotates while emitting X-rays by an X-ray tube, and collects projection data for a scanning region including a first region and a second region, the phantom for the calibration not existing in the first region and existing in the second region, a discriminating unit that discriminates first data for an air region and second data for a calibration phantom region from the collected projection data, on the basis of a predetermined reference, and a data creating unit that creates correction data on the basis of the first data and the second data that are discriminated by the discriminating unit.

According to another aspect of the invention, it is provided an X-ray CT apparatus including a projection data collecting unit that continuously moves a ceiling plate mounting a calibration phantom and continuously rotates while emitting X-rays by an X-ray tube, and collects projection data for a scanning region including a region where the calibration phantom exists, and a data creating unit that creates correction data on the basis of the collected projection data.

According to yet another aspect of the invention, it is provided a method of creating correction data for X-ray CT including continuously moving a ceiling plate mounting a water phantom and continuously rotating while emitting X-rays by an X-ray tube so as to collect projection data for a scanning region including a first region and a second region, the water phantom not existing in the first region but existing in the second region, discriminating air data for an air region and water data for a water region for a calibration phantom region from the collected projection data, on the basis of a predetermined reference, and creating correction data on the basis of the air data and the water data that are discriminated by the discriminating.

According to yet another aspect of the invention, it is provided a method of creating correction data for X-ray CT including continuously moving a ceiling plate mounting a water phantom and continuously rotates while emitting X-rays by an X-ray tube so as to collect projection data for a scanning region including a region where the water phantom exists, and creating correction data on the basis of the collected projection data.

BRIEF DESCRIPTION OF THE SEVERAL VIEWS OF THE DRAWING

FIG. 2D is a diagram illustrating the correspondence relationships between a timing of acquiring correction data on 360° and a detecting viewing angle in a predetermined channel for each column number;

FIG. 6 is a flowchart illustrating the flow of a correction data creating process that uses helical scanning according to an embodiment of the invention.

DETAILED DESCRIPTION OF THE INVENTION

Figure 1:
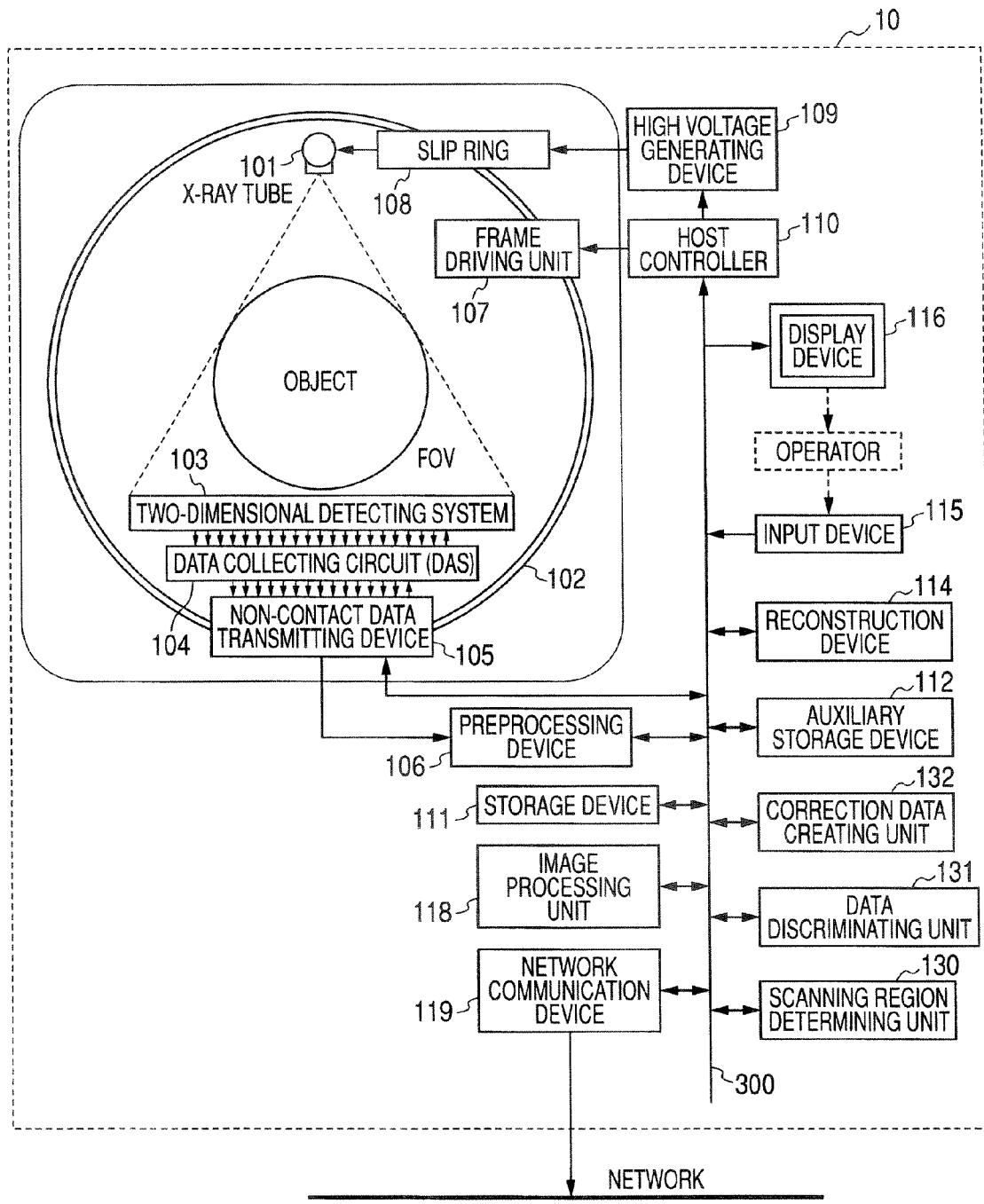
FIG. 1 is a block diagram illustrating a structure of an X-ray CT apparatus according to an embodiment of the invention.

Hereinafter, first and second embodiments of the invention will be described with reference to the accompanying drawings. In the description below, components having almost the same functions and structures are denoted by the same reference numerals, and the overlapping description is made, only if necessary.

Further, the description is given of the case where water as a medium is filled into a phantom for calibration (that is, the case of a water phantom). However, the invention is not limited thereto. The medium that is filled into the phantom for calibration is not limited to a specific one, as long as the medium has approximately the same X-ray absorptance as the water. For example, when the photon counting number is small, it is possible to use a phantom for calibration (polypropylene phantom) that is made of polypropylene whose X-ray absorptance is smaller than that of the water.

First Embodiment

Hereinafter, an X-ray CT apparatus according to a first embodiment of the invention will be described with reference to the accompanying drawings. Types of the X-ray CT apparatus may include a rotational/rotational type where one X-ray tube and one X-ray detector are provided, and rotate around a subject, and a stationary/rotational type where a plurality of detecting elements are disposed in a ring shape and only an X-ray tube rotates around a subject. The invention may be applied to both the rotational/rotational type and the stationary/rotational type. In this case, the rotational/rotational type that has been mainly used in recent times will be described.

Further, when reconstructing tomographic image data that corresponds to one slice, projection data that corresponds to one cycle around the subject, that is, approximately 360° is necessary, and even in a half scanning method, projection data that corresponds to 180°+a viewing angle is necessary. Even in all of the reconstruction methods, the invention may be applied. In this embodiment, the former is exemplified.

In recent years, X-ray CT apparatuses where a plurality of pairs of X-ray tubes and X-ray detectors are mounted on a rotation frame, that is, so-called multi-tube-type X-ray CT apparatuses are manufactured, and associated technologies thereof have been developed. The invention may be applied to both a one-tube-type X-ray CT apparatus according to the related art and a multi-tube-type X-ray CT apparatus. In this embodiment, the one-tube-type X-ray CT apparatus is exemplified.

FIG. 1 is a block diagram illustrating a structure of an X-ray CT apparatus according to a first embodiment of the invention. An X-ray CT apparatus 10 includes an X-ray tube 101, a rotation frame 102, a two-dimensional detecting system 103, a data collecting circuit 104 (DAS), a non-contact data transmitting device 105, a preprocessing device 106, a frame driving unit 107, a slip ring 108, a high voltage generating device 109, a storage device 111, an auxiliary storage device 112, a reconstructing device 114, an input device 115, a display device 116, an image processing device 118, a network communication device 119, a host controller 110, and a data/control bus 300.

The X-ray tube 101 is a vacuum tube that generates X rays, and is provided in the rotation ring 102. The X-ray tube 101 is supplied with power (a tube current and a tube voltage) necessary for X-ray emission from the high voltage generating device 109 through the slip ring 108. The X-ray tube 101 accelerates electrons with the supplied high voltage so as to collide the electrons with a target, and thus emits the X-rays to the subject loaded in a field of view (FOV).

Further, a collimator (not shown), which shapes an X-ray beam emitted from the X-ray tube into a cone shape (rectangular cone shape) or a fan beam shape, is provided between the X-ray tube 101 and the subject.

The X-ray tube 101 and the two-dimensional detecting system 103 are provided in the rotation ring 102. The rotation ring 102 is driven by the frame driving unit 107, and rotations around the subject at a high speed, for example, one second or less per one rotation, together with the X-ray tube 101 and the two-dimensional detecting system 103.

The two-dimensional detecting system 103 is a detecting system that detects the X rays having transmitted the subject, and is attached to the rotation ring 102 in a direction opposite to the X-ray tube 101. In the two-dimensional detecting system 103, a plurality of detecting elements, each of which is formed by combining a scintillator and a photodiode, are disposed in a matrix in regards to a longitudinal direction (slice direction) of a bed mounting the subject and a channel direction orthogonal to the longitudinal direction of the bed. In this case, for example, in regards to the channel direction, almost a thousand of (a thousand of channels of) detecting elements are disposed (hereinafter, in arrangement of a thousand of detecting elements, one column in regards to the channel direction is referred to as a 'detecting element column').

Further, as a method of converting an incident X ray into a charge in the detecting elements, there are a direct converting method and an indirect converting method. The direct converting method uses generation of electron and hole pairs in a semiconductor by the X ray and movement of the electron and hole pairs to electrodes, that is, a photoelectric effect. Meanwhile, the indirect converting method converts the X ray into light by using a fluorescent body, such as the scintillator, and converts the light into a charge by using a photoelectric conversion element, such as the photodiode. The X-ray detecting element may be applied to both the direct converting method and the indirect converting method.

The data collecting circuit 104 (DAS) includes a plurality of data collecting element columns where DAS chips are disposed. The data collecting circuit 104 receives a large amount of data (raw data) with respect to all of the channels of M×N that are detected by the two-dimensional detecting system 103, performs an amplifying process, an A/D converting process, and the like on the data, and collectively transmits the data to a fixed-side data processing unit through the non-contact data transmitting device 105 to which optical communication is applied.

The non-contact data transmitting device 105 optically transmits the collected X ray transmitting data to a next-stage device. In the two-dimensional detecting system 103, in order to transmit to the non-contact data transmitting device 105 or the DAS 104 a large amount of two-dimensional data created at a high speed without time delay, a high speed process is performed thereon.

The preprocessing device 106 receives data created by the DAS 104 through the non-contact data transmitting device 105, and executes sensitivity correction or X-ray strength correction on the received data. The raw data on 360° that is subjected to various correction processes is temporarily stored in the storage device 111. Further, the raw data that is subjected to the preprocessing by the preprocessing device 106 is called 'projection data'.

The frame driving unit 107 performs driving control that integrally rotates the X-ray tube 101 and the two-dimensional detecting system 103 around a central axis parallel to a body axis direction of the subject that is inserted into an opening for diagnosis.

The high voltage generating device 109 supplies power necessary for X-ray emission to the X-ray tube 101 through the slip ring 108, and includes a high voltage converter, a filament heating converter, a rectifier, a high voltage switch, and the like. The high voltage generating device 109 supplies the high voltage to the X-ray tube 101 by the slip ring 108.

The host controller 110 controls various processes, such as a photographic process, a data process, and an image process. For example, in the photographic process, the host controller 110 stores scanning conditions, such as the previously input slice thickness, in an internal memory, and controls the high voltage generating device 109, a bed driving unit (not shown), the frame driving unit 107, a movement amount of the bed in the body axis direction, and a movement speed of the bed, the rotation speed and the rotation pitch of each of the X-ray tube 101 and the two-dimensional detecting system 103, an emission timing of the X ray, and the like, on the basis of scanning conditions automatically set by using patient IDs or the like (or scanning conditions directly set by the input device 115 in a manual mode). Further, the host controller 110 emits the X-ray cone beam or the X-ray fan beam onto a predetermined projection region of the subject in a plurality of directions, and performs a photographic process on the X-ray CT image.

Furthermore, the host controller 110 performs control on the correction data creation using the helical scanning, which will be described in detail below.

The storage device 111 stores image data, such as raw data, projection data, and tomographic image data, a program for a test plan, and a dedicated program that realizes the correction data creation using the helical scanning.

The auxiliary storage device 112 has a large capacity of storage region that can store the reconstructed image data that is created by the reconstructing device 114.

The reconstructing device 114 performs a reconstructing process on the projection data on the basis of predetermined reconstruction parameters (a reconstruction region size, a reconstruction matrix size, a threshold value for extracting a target portion, and the like), and creates a reconstructed image data that corresponds to a predetermined slice.

The input device 115 includes a keyboard, various switches, a mouse, and the like, and can input various scanning conditions, such as the thickness of the slices and the number of the slices, through the operator.

The image processing unit 118 performs an image process for display, such as a window conversion process and an RGB process, on the reconstructed image data that is created by the reconstructing device 114, and outputs the process result to the display device 116. Further, the image processing unit 118 creates a so-called pseudo 3D image, such as a tomographic image of an arbitrary section, a projection image from an arbitrary direction, and a three-dimensional surface image, on the basis of the instruction of the operator, and outputs it to the display device 116. The output image data is displayed as an X-ray CT image on the display device 116.

The network communication device 119 exchanges the raw data with the data managing system 15 through the network.

The scanning region determining unit 130 determines a scanning region including a water region and an air region on the basis of the positional information obtained by the positioning scanning process. In this case, the air region refers to a region where only air is allowed to exist between the X-ray tube 101 and the two-dimensional detecting system 103, and the data collection is performed. Further, the water region refers to a region where a phantom filled with the water is allowed to exist between the X-ray tube 101 and the two-dimensional detecting system 103, and the data collection is performed.

The data discriminating unit 131 discriminates the data obtained by scanning the scanning region as data for the air region (air data) and data for the water region (water data) on the basis of a predetermined reference.

The correction data creating unit 132 creates correction data for converting X-ray absorptance of the tissues, such as the internal organs, into a CT value, on the basis of the discriminated air and water data.

Further, the data processes, such as the image reconstruction and the section conversion, the display operation, the discrimination between the air data and the water data, and the correction data creating process based on the discrimination between the air data and the water data, which are performed after collecting scanning data, are generally performed in the X-ray CT apparatus 10. However, an image processing apparatus separate from the X-ray CT apparatus may be provided such that the image processing apparatus may perform the above-described various processes executed after collecting the data. Function of creating correction data using helical scanning Next, a function of creating the correction data of the X-ray CT apparatus that creates correction data using the helical scanning will be described. According to this function, the helical scanning process is performed on the phantom mounted on the bed to allow correction data acquisition by the relatively short phantom, and allow air and water data acquisition by a one-time scanning sequence.

Figure 2A:
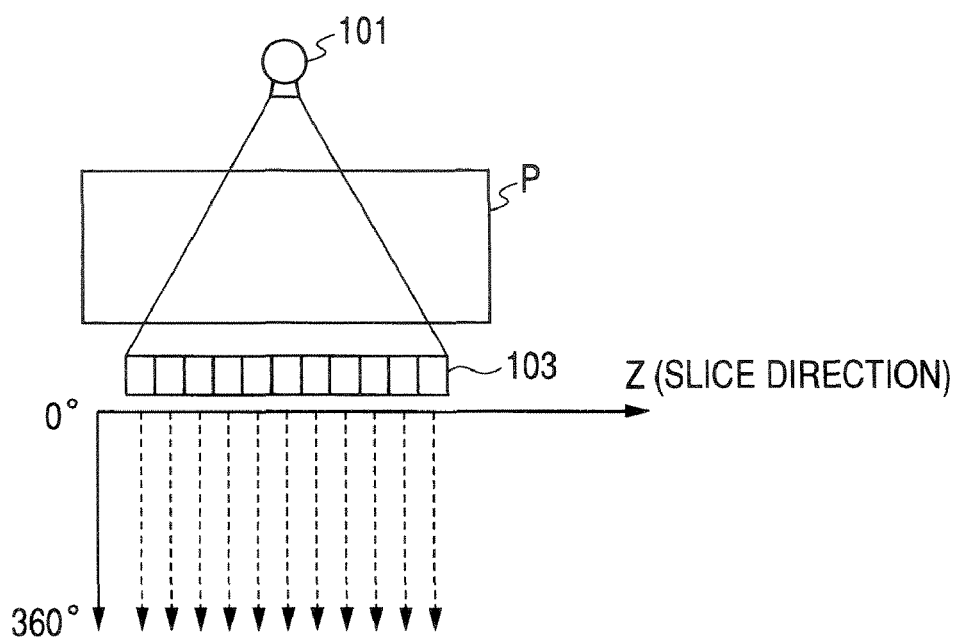
FIG. 2A is a diagram illustrating a method of collecting water data according to the related art that uses conventional scanning.
Figure 2B:
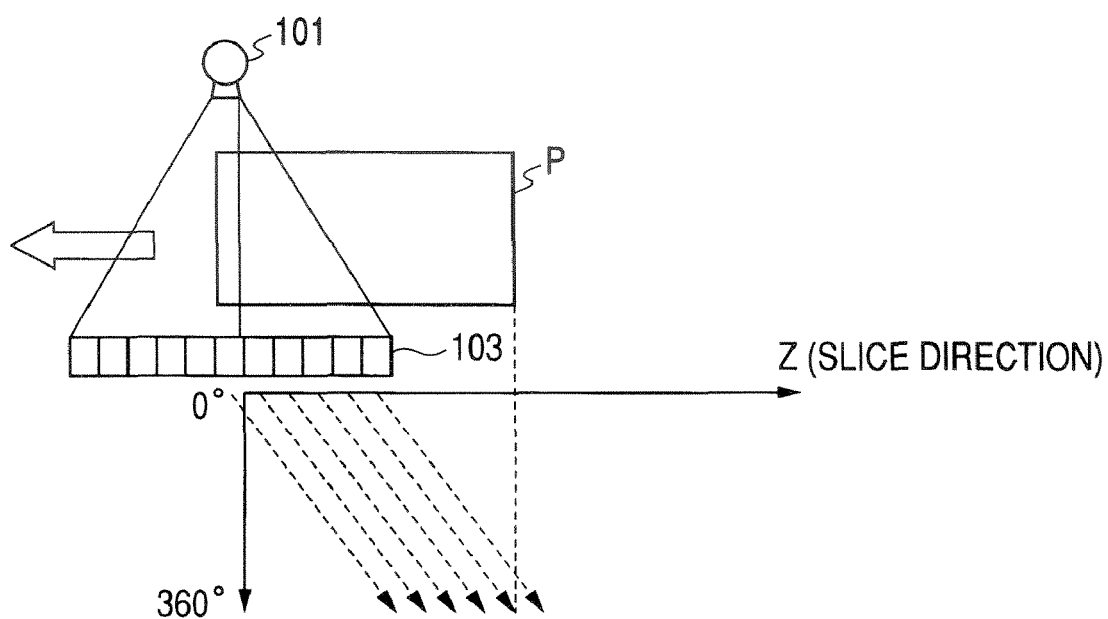
FIG. 2B is a diagram illustrating a method of collecting water data using a correcting and collecting function.

FIG. 2A is a diagram illustrating a method of collecting water data using conventional scanning according to the related art. FIG. 2B is a diagram illustrating a method of collecting water data using the function of correcting and collecting data. Generally, when the correction data is collected, water data for a phantom P by one-time rotation is necessary. In the method of collecting data according to the related art shown in FIG. 2A, even when the X-ray tube 101 rotates once, the relatively positional relationships between the two-dimensional detecting system 103 and the phantom P is not changed. For this reason, the phantom P needs to have a size according to the number of the detecting element columns.

Meanwhile, in the method using the function of correcting and collecting data shown in FIG. 2B, the helical scanning process is performed on the phantom while the bed is moved, and thus the data of the phantom by one rotation is collected while the relatively positional relationship between the two-dimensional detecting system 103 and the phantom is changed. Accordingly, according to the function of correcting and collecting the data, for example, in the case of when a 360° interpolation method is used, if the bed moving speed is set to V and the time necessary when the X-ray tube 101 and the two-dimensional detecting system 103 rotate by 360° is set to T, the total length L of the phantom may be at least not less than VT. Further, if the total length L of the phantom is almost half the length of the detecting element column in a slice direction (column direction), it is possible to obtain appropriate correction data.

Figure 2C:
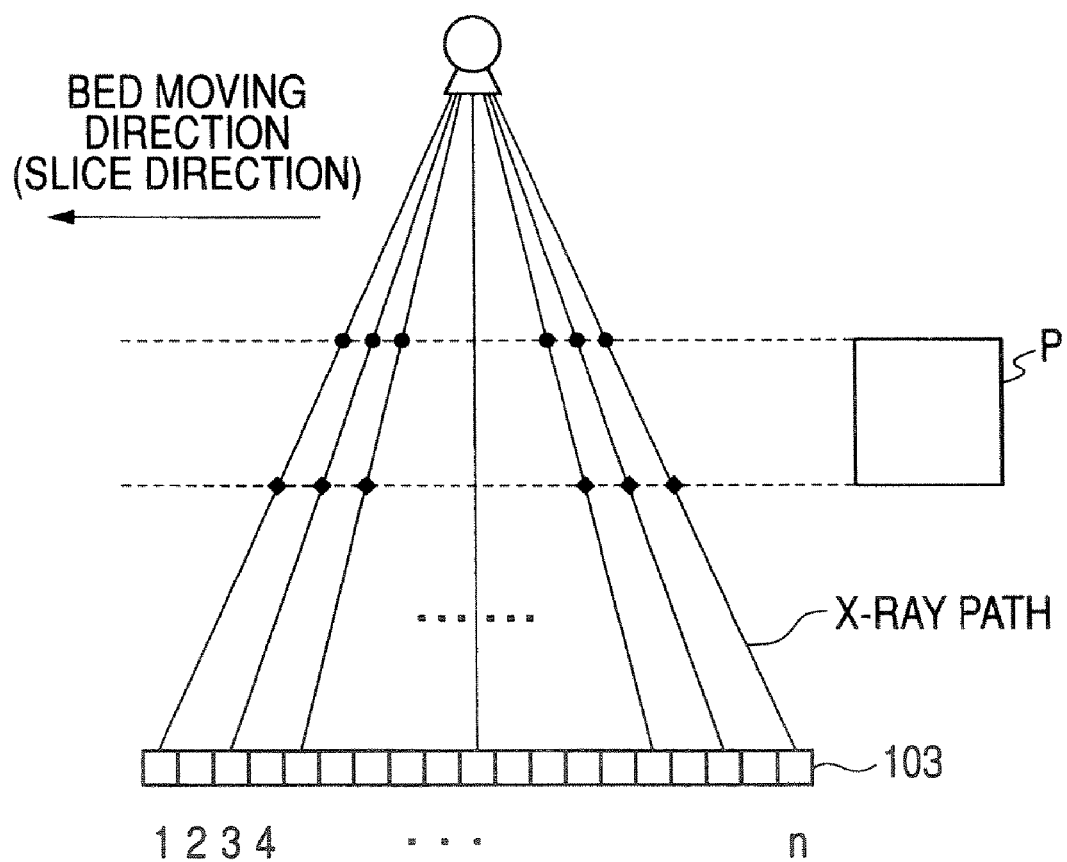
FIG. 2C is a diagram illustrating an aspect of when a phantom P enters into an X-ray emitting region in helical scanning.

Further, as shown in FIG. 2C, when the correction data is created using the function of correcting and collecting data, the phantom P moves in a slice direction by the bed, and enters into the X-ray irradiating region (region where an X-ray path exists) from the n-th column of a detecting element side. For this reason, on the two-dimensional detecting system 103 (that is, multi-column detector), the phantom may not exist between an arbitrary detecting element column and the X-ray tube (therefore, only the air exists), and the phantom may exist between an arbitrary detecting element column and the X-ray tube.

FIG. 2D is a diagram illustrating the correspondence relationships between an acquiring timing and a detecting viewing angle of the correction data on 360° in a predetermined channel for each column number. As shown in FIG. 2D, when data (water data) that is obtained by detecting the X ray having passed the water region of the phantom is detected on 360° for each detecting element through the helical scanning accompanied with the bed movement, the detecting start timing (or viewing angle of when the detection starts) is different for each column number of the detecting element.

Meanwhile, in the method of collecting the water data through the conventional scanning according to the related art shown in FIG. 2A, since the bed does not move, when the scanning is performed, the X-ray paths that correspond to all of the detecting elements pass through the inner region (water region) of the phantom at substantially the same timing. Accordingly, when the water data by 360° is detected using the method according to the related art, the detecting start timing (or viewing angle of when the detection starts) is the same in all of the detecting element columns.

Further, when the data (air data) that is obtained by detecting the X ray passing through only the air region is acquired, the detecting start timing (or viewing angle of when the detection starts) does not cause a problem. For example, it is possible to acquire the data by cutting and extracting arbitrary data on 360° from the projection data that is detected before the phantom P enters into the X-ray path for each detecting element column.

Generally, when performing helical scanning, the bed moving position or the positional information obtained by the positioning scanning and the viewing angle can be associated with each other. Accordingly, the air data and the water data are discriminated on the basis of the positional information that is obtained by the positioning scanning, and thus it is possible to acquire the air data and the water data for each detecting element column through a one-time scanning sequence. Further, the positional information means the correspondence relationship between the position on the scanogram obtained by the positioning scanning and the data collecting position assigned to the collected data (that is, a numerical value of a rotary encoder indicating the bed position at which data is collected).

Further, in collecting the correction data in the X-ray CT apparatus according to the related art, NRA collection and Air collection are performed. In collecting the NRA, the water data $Water_0$ for the phantom P by one rotation is collected by performing conventional scanning at a predetermined rotation speed (for example, 0.75 s per rotation). Further, in a state where the phantom P does not exist, the air data $Air_0$ is collected by performing the conventional scanning at the same rotation speed while using the sequence different from the sequence used when the water data is collected. Meanwhile, in the case of the Air collection, in order to correct the difference in the rotation speed at the time of scanning, the air data $Air_t$ is collected at each rotation speed (for example, 1.0 s per rotation, and 0.5 s per rotation). Using the data obtained by each sequence, the difference in the rotation speed is corrected by the following Equation (1).

$$NRA = Water_0 \times (Air_t/Air_0) \qquad (1)$$

In collecting the NRA, the function of creating the correction data using the helical scanning allows to collect the water data $Water_0$ and the air data $Air_0$ through a one-time sequence.

Operation

Next, the operation of the X-ray CT apparatus 1 will be described.

Figure 3:
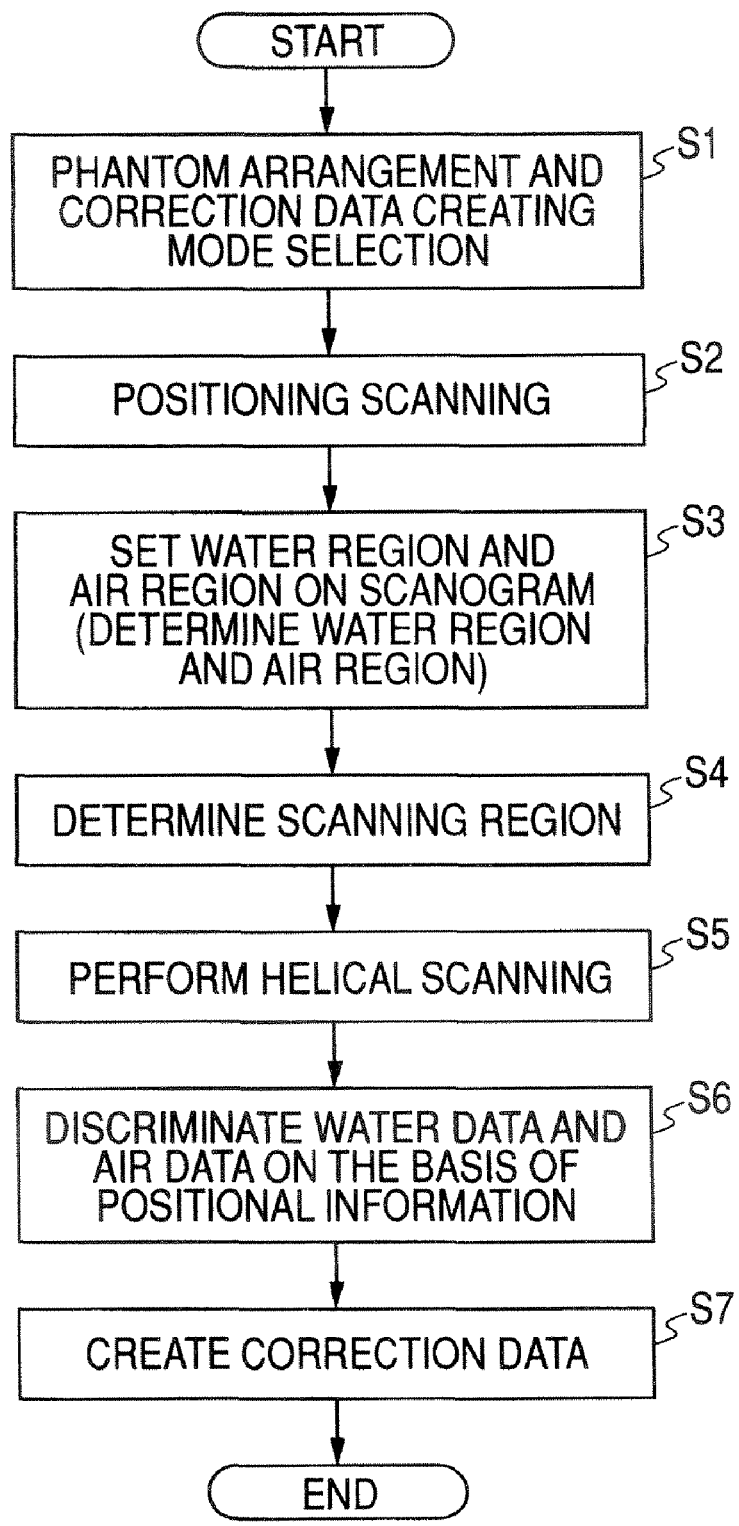
FIG. 3 is a flowchart illustrating the flow of a correction data creating process that uses helical scanning.

FIG. 3 is a flowchart illustrating the flow of the process according to the function of creating the correction data using the helical scanning (a correction data creating process using the helical scanning). As shown in FIG. 3, first, the arrangement of the phantom on the bed, and the selection of the correction data creating mode through the input device 115 are executed (STEP S1). The host controller 110 executes the positioning scanning operation in response to the selection operation of the correction data creating mode (STEP S2). The image that is acquired by the positioning scanning operation is displayed in a predetermined form as a scanogram in the display device 116. The water data collecting region and the air data collecting region are determined by the scanogram that is input by the input device 115 and is displayed on the display device (STEP S3).

Figure 4:
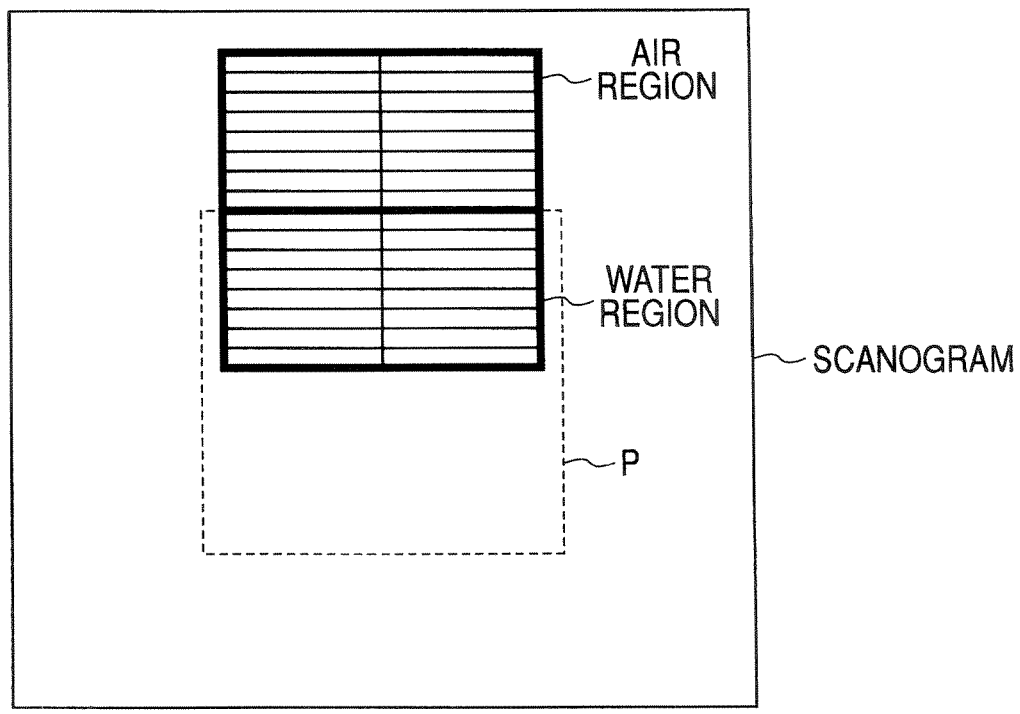
FIG. 4 is a diagram illustrating an example of a method of designating a water data collecting region and an air data collecting region on a scanogram.

FIG. 4 is a diagram illustrating an example of an input sequence of the water data collecting region and the air data collecting region on the scanogram. By using the input device 115, the operator sets the water data collecting region to the image region corresponding to the phantom P, and sets the air data collecting region to the image region where the phantom P does not exist, as shown in FIG. 4. The host controller 110 determines the positions of the water data collecting region and the air data collecting region on the basis of the respective regions set on the scanogram.

Next, the scanning region determining unit 130 determines a scanning region as a region where scanning needs to be performed in order to reconstruct the water data collecting region and the air data collecting region (STEP S4). The host controller 110 executes the helical scanning, and collects the data for the determined scanning region (STEP S5).

Next, on the basis of the position data of the water data collecting region and the air data collecting region designated in step S3, the data discriminating unit 131 discriminates the data for the collected scanning region as the water data and the air data (STEP S6). The correction data creating unit 132 creates the correction data for converting the X-ray absorptance of the tissues of the internal organs into CT values setting water to 0 and air to −1000, on the basis of the discriminated water and air data (STEP S7).

According to the above-described structure, the following effects can be obtained.

According to the X-ray CT apparatus of the first embodiment, the helical scanning process is performed on the phantom mounted on the bed so as to obtain the water data, and creates the correction data on the basis of the obtained data. Accordingly, as compared with the related art, it is possible to acquire the correction data by the relatively short phantom.

Further, according to the X-ray CT apparatus of the first embodiment, it is possible to discriminate the collecting region of the water data and the collecting region of the air data from the data collected on the basis of the positional information of the water region and the air region set on the scanogram. Accordingly, by using the discriminated water and air data, the correction data can be created through the one-time sequence.

Second Embodiment

Next, a second embodiment of the invention will be described. An X-ray CT apparatus according to the second embodiment uses the difference between the X-ray absorptance of the water and the X-ray absorptance of the air (that is, the difference in the photon counting number) on the basis of the discrimination between the air data and the water data.

Figure 5:
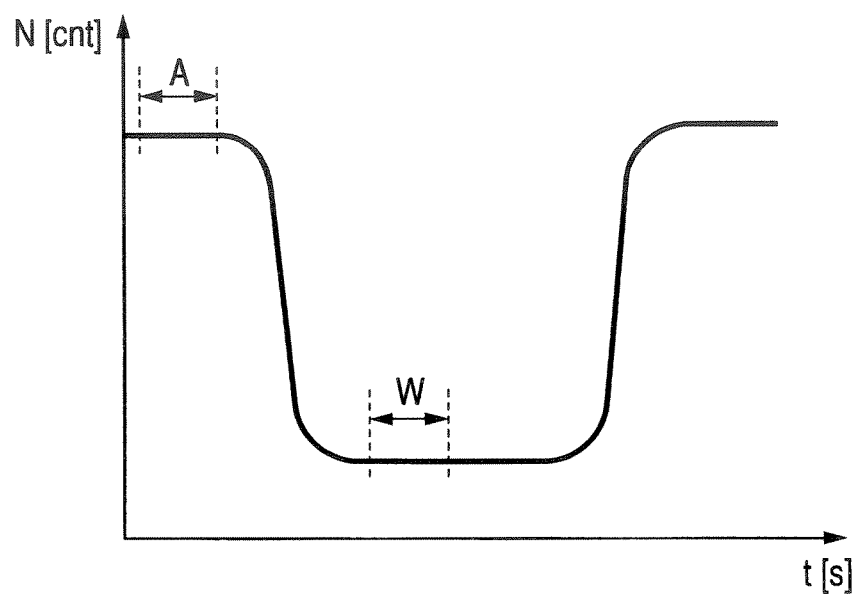
FIG. 5 is a diagram illustrating an example of an output profile that is obtained by performing helical scanning on a scanning region including a water region and an air region and is obtained from an arbitrary detecting element column from a detecting system 103.

FIG. 5 is a diagram illustrating a discriminating operation between the air data and the water data according to the second embodiment, which illustrates an example of an output profile that is obtained by performing the helical scanning on the scanning region including the water region and the air region and is obtained from an arbitrary detecting element of an arbitrary column from the two-dimensional detecting system 103. In FIG. 5, a horizontal axis indicates a time. However, the positional relationship between the phantom and the two-dimensional detecting system 103 is the same because the moving speed of the bed on which the phantom P is mounted is constant during the helical scanning process. Further, reference character W indicates a region that corresponds to the water data on 360°, and reference character A indicates a region that corresponds to the air data on 360°.

As shown in FIG. 5, in the air region and the water region, the obtained output values are different from each other (that is, the photon counting number). Accordingly, as shown in FIG. 5, it is possible to discriminately obtain the water data and the air data necessary when creating the correction data for each detecting element by obtaining the output profiles from all of the detecting elements and on the basis of the difference between the air region and the water region in the counting number.

Next, the operation of the X-ray CT apparatus 1 according to the second embodiment will be described.

FIG. 6 is a flowchart illustrating the flow of the correction data creating process using the helical scanning according to the second embodiment. As shown in FIG. 6, after arranging the phantom on the bed and selecting the correction data creating mode through the input device 115, the positioning scanning process is executed (STEPS S11 and S12). By using the scanogram that is obtained by the positioning scanning process, the water data collecting region and the air data collecting region are determined by the input from the input device 115 (STEP S13), and the scanning region is determined (STEP S14). The host controller 110 executes the helical scanning, and collects the data for the determined scanning region (STEP S15).

Next, the data discriminating unit 131 discriminates the collected data for the scanning region as the water data (data of the counting number Na in FIG. 5) and the air data (data of the counting number Nw in FIG. 5) on the basis of the photon counting number (STEP S16). Further, the data discriminating unit 131 extracts the data corresponding to the period W from the discriminated water data and extracts the data corresponding to the period A from the air data discriminated in the same manner, for creating the correction data.

Next, the correction data creating unit 132 creates the correction data for converting the X-ray absorptance of the tissues of the internal organs into CT values setting water to 0 and air to −1000, on the basis of the extracted water and air data (STEP S17)

According to the above-described structure, the same effects as the first embodiment can be obtained.

Further, the invention is not limited to the above-described embodiments, and the components may be modified and specified without departing from the sprit and scope thereof in embodied stages. For specified modifications, for example, they are as follows.

(1) The respective functions according to the respective embodiments can be achieved by installing the program executing the corresponding process in a computer such as a work station, and developing the program on the memory. At this time, the program that can execute the above-described method by the computer can be stored in a storage medium, such as a magnetic disk (a floppy disk®, a hard disk, and the like), an optical disk (a CD-ROM, a DVD, and the like), and a semiconductor memory.

(2) In collecting the data of the scanning region including the water region and the air region, if the necessary data can be collected, there are not limits in the timings of the X-ray irradiation and the data collection. For example, when performing continuous helical scanning once, the X-ray irradiation and the data collection may start at a timing when the scanning region reaches the location on the detecting element column with the movement of the bed. Further, the DAS may be controlled such that the X-ray irradiation starts from the front stage of the scanning region, and the data collection starts at the timing when the scanning region reaches the location on the detecting element column.

(3) In the above-described embodiments, the examples when the air data and the water data are collected by using the one-time scanning sequence are exemplified. However, the invention is not limited thereto. For example, only the water data may be collected by using helical scanning, if necessary. In this case, for example, only the water region may be set on the scanogram, and the scanning region may be so determined that the set water region is included.

Further, various modifications can be made by approximately combining the plurality of components disclosed in the above-described embodiments. For example, some components may be removed from all of the components disclosed in the above-described embodiments. Further, components according to another embodiment may be approximately combined.

What is claimed is:

1. An X ray CT apparatus comprising:
    a projection data collecting unit that exerts a helical scanning by rotating an X-ray tube around a rotational axis and moving a calibration object along the rotational axis simultaneously and continuously and collects projection data for a scanning region including a first region where the calibration object does not exist and a second region where the calibration object exists during the continuous helical scanning;
    a discriminating unit that discriminates the projection data collected from the first region as first data and the projection data collected from the second region as second data, based on a predetermined reference; and
    a data creating unit that creates correction data based on the first data and the second data.

2. The X ray CT apparatus according to claim 1, further comprising:
    a setting unit that sets the first region and the second region on a positioning image that is obtained by positioning scanning executed before collecting the projection data, wherein the discriminating unit discriminates the first data and the second data based on the a relationship between the first region and the second region of the positioning image and positions at which the projection data are collected.

3. The X ray CT apparatus according to claim 1, wherein the discriminating unit discriminates the first data and the second data on the basis of the difference between X ray absorptance of a medium filled into the calibration object and X ray absorptance of the air.

4. The X ray CT apparatus according to claim 1, wherein water is filled into the calibration object, and the discriminating unit discriminates the first data and the second data from the collected projection data.

5. The X ray CT apparatus according to claim 1, wherein polypropylene is filled into the calibration object, and
the discriminating unit discriminates the first data and the second data from the collected projection data.

6. An X ray CT apparatus comprising:
a projection data collecting unit that exerts a helical scanning by rotating an X-ray tube around a rotational axis and moving a calibration object along the rotational axis simultaneously and continuously, and collects projection data for a scanning region including a first region where the calibration object does not exist and a second region where the calibration object exists during the continuous helical scanning; and
a data creating unit that creates correction data based on the collected projection data.

7. The X ray CT apparatus according to claim 6, wherein water is filled into the calibration object, and the data creating unit creates the correction data based on the water-filled calibration object.

8. The X ray CT apparatus according to claim 6, wherein polypropylene is filled into the calibration object, and
the data creating unit creates the correction data based on the polypropylene-filled calibration object.

9. The X ray CT apparatus according to claim 1, wherein the projection data collecting unit further includes a detector including a plurality of detecting elements for detecting X rays, disposed in a same direction as movement of the calibration object, and
the discriminating unit discriminates the first data and the second data from the collected projection data based on X ray paths detected by the plurality of detecting elements.

10. The X ray CT apparatus according to claim 9, wherein the discriminating unit selects a column of detecting elements from the plurality of detecting elements for detecting the second data, such that the second data is created using X rays incident from a surface of the calibration object according to a direction of movement of the source and emitted from a surface of the calibration phantom according to a direction of movement of the detector.

11. A method of creating correction data for X ray CT, the method comprising:
continuously moving a water-filled calibration object along a rotational axis and continuously rotating a source emitting X rays by an X ray tube around the rotational axis, simultaneously, so as to collect projection data for a scanning region including a first region where the water-filled calibration object does not exist and a second region where the water-filled calibration object exists during the continuous helical scanning;
discriminating the projection data collected from the first region as first data and the projection data collected from the second region as second data, based on a predetermined reference; and
creating correction data based on the first data and the second data.

12. A method of creating correction data for X ray CT, the method comprising:
continuously moving a water-filled calibration object along a rotational axis and continuously rotating a source emitting X rays by an X ray tube around the rotational axis, simultaneously, so as to collect projection data for a scanning region including a first region where the water-filled calibration object does not exist and a second region where the calibration object exists during the continuous helical scanning; and
creating correction data based on the collected projection data.

* * * * *